(12) United States Patent
Van Der Werf et al.

(10) Patent No.: US 7,453,577 B2
(45) Date of Patent: Nov. 18, 2008

(54) APPARATUS AND METHOD FOR INSPECTING A PATTERNED PART OF A SAMPLE

(75) Inventors: Jan Evert Van Der Werf, Waalre (NL); Arie Jeffrey Den Boef, Waalre (NL); Cristian-Nicolae Presura, Veldhoven (NL)

(73) Assignee: ASML Netherlands B.V., Veldhoven (NL)

( * ) Notice: Subject to any disclaimer, the term of this patent is extended or adjusted under 35 U.S.C. 154(b) by 263 days.

(21) Appl. No.: 11/010,566

(22) Filed: Dec. 14, 2004

(65) Prior Publication Data

US 2006/0126074 A1    Jun. 15, 2006

(51) Int. Cl.
*G01B 11/30* (2006.01)
(52) U.S. Cl. .................................. 356/495; 356/516
(58) Field of Classification Search ......... 356/485–490, 356/492–495, 496–499, 508–510, 516, 520, 356/521, 369
See application file for complete search history.

(56) References Cited

U.S. PATENT DOCUMENTS

| | | | | |
|---|---|---|---|---|
| 4,844,616 A * | 7/1989 | Kulkarni et al. | ............. | 356/495 |
| 5,420,717 A * | 5/1995 | Tabata | ............. | 359/371 |
| 5,699,160 A * | 12/1997 | Barenboim et al. | ......... | 356/495 |
| 5,703,692 A | 12/1997 | McNeil et al. | ............. | 356/445 |
| 5,880,838 A | 3/1999 | Marx et al. | ............. | 356/351 |
| 5,898,500 A * | 4/1999 | Canteloup et al. | ........... | 356/492 |
| 5,914,782 A * | 6/1999 | Sugiyama | ............. | 356/491 |
| 5,963,329 A | 10/1999 | Conrad et al. | ............. | 356/372 |
| 6,134,012 A | 10/2000 | Aspnes et al. | | |
| 6,141,103 A | 10/2000 | Pinaton et al. | | |
| 6,256,097 B1 | 7/2001 | Wagner | | |
| 6,259,530 B1 * | 7/2001 | Monsallut | ............. | 356/487 |
| 6,411,389 B1 | 6/2002 | Rushford | | |
| 6,608,690 B2 | 8/2003 | Niu et al. | ............. | 356/635 |
| 6,633,389 B1 * | 10/2003 | Poris et al. | ............. | 356/513 |
| 6,690,473 B1 * | 2/2004 | Stanke et al. | ............. | 356/601 |
| 6,699,624 B2 | 3/2004 | Niu et al. | ............. | 430/5 |
| 6,704,661 B1 | 3/2004 | Opsal et al. | ............. | 702/27 |
| 6,721,691 B2 | 4/2004 | Bao et al. | ............. | 702/189 |
| 6,738,138 B2 | 5/2004 | Wei | ............. | 356/369 |
| 6,753,961 B1 | 6/2004 | Norton et al. | ............. | 356/364 |

(Continued)

FOREIGN PATENT DOCUMENTS

WO    WO02/052350 A1    7/2002

(Continued)

OTHER PUBLICATIONS

IBM Technical Disclosure Bulletin, vol. 34, No. 10A, Mar. 1992, pp. 140-143.*

(Continued)

*Primary Examiner*—Samuel A Turner
(74) *Attorney, Agent, or Firm*—Sterne, Kessler, Goldstein & Fox P.L.L.C

(57) ABSTRACT

An inspection apparatus is disclosed having an radiation system configured to provide an radiation beam, a beamnsplitter configured to create, from the radiation beam, a first illumination beam and a second illumination beam directed to a planar reference part of a sample and a patterned part of the sample, respectively, and a beam detector configured to detect a detection beam, the detection beam comprising a recombination of radiation scattered from the planar reference part and the patterned part.

30 Claims, 2 Drawing Sheets

U.S. PATENT DOCUMENTS

| | | | |
|---|---|---|---|
| 6,768,983 B1 | 7/2004 | Jakatdar et al. | 706/46 |
| 6,772,084 B2 | 8/2004 | Bischoff et al. | 702/127 |
| 6,785,638 B2 | 8/2004 | Niu et al. | 702/189 |
| 6,813,034 B2 | 11/2004 | Rosencwaig et al. | 356/601 |
| 6,819,426 B2 | 11/2004 | Sezginer et al. | 356/401 |
| 6,856,408 B2 | 2/2005 | Raymond | 356/601 |
| 6,919,964 B2 | 7/2005 | Chu | 356/601 |
| 6,928,628 B2 | 8/2005 | Seligson et al. | 716/4 |
| 6,972,852 B2 | 12/2005 | Opsal et al. | 356/625 |
| 6,974,962 B2 | 12/2005 | Brill et al. | 250/548 |
| 6,987,572 B2 | 1/2006 | Lakkapragada et al. | 356/601 |
| 7,046,376 B2 | 5/2006 | Sezginer | 356/601 |
| 7,061,615 B1 | 6/2006 | Lowe-Webb | 356/401 |
| 7,061,623 B2 | 6/2006 | Davidson | 356/497 |
| 7,061,627 B2 | 6/2006 | Opsal et al. | 356/601 |
| 7,068,363 B2 | 6/2006 | Bevis et al. | 356/237.5 |
| 2002/0192577 A1 | 12/2002 | Fay et al. | |
| 2004/0085537 A1* | 5/2004 | Ausserre et al. | 356/369 |
| 2004/0119970 A1 | 6/2004 | Dusa et al. | 356/237.1 |
| 2004/0207849 A1 | 10/2004 | Nikoonahad et al. | |
| 2006/0033921 A1 | 2/2006 | Den Boef et al. | 356/446 |
| 2006/0066855 A1 | 3/2006 | Den Boef et al. | 356/401 |
| 2006/0139592 A1 | 6/2006 | Den Boef et al. | 355/53 |

FOREIGN PATENT DOCUMENTS

| | | |
|---|---|---|
| WO | WO02/052351 A1 | 7/2002 |
| WO | WO 2004/023071 A1 | 3/2004 |

OTHER PUBLICATIONS

Optical Shop Testing, Malacara, 1992, pp. 99-102.*

McGraw Hill Concise Encyclopedia of Science and Technology, 1998, p. 1846.*

Lessor et al, Quantitive surface topography determination by Nomarski reflection microscopy, Journal OSA, vol. 69, No. 2, Feb. 1979, pp. 357-366.*

Boher, P. et al, "A New Purged UV Spectroscopic Ellipsometer to Characterize Thin Films and Multilayers at 157 nm", *Proc. Of SPIE*, Mar. 2000, vol. 3998, pp. 379-389.

Burge, D.K. et al., "Effect of a Thin Surface Film on the Ellipsometric Determination of Optical Constants," *Journal of the Optical Society of America*, Jun. 1964, vol. 54, pp. 1428-1433.

Niu, X. et al., "Specular Spectroscopic Profilometry for the Sub-0.18 µm PolySi-Gate Processes," *Proc. Of SPIE*, Mar. 2000, vol. 3998, pp. 846-855.

Raymond, C. et al., "Multiparameter grating metrology using optical scatterometry," *J. Vac. Sci. Technol.*, Mar./Apr. 1997, B 15(2), pp. 361-368.

* cited by examiner

APPARATUS AND METHOD FOR INSPECTING A PATTERNED PART OF A SAMPLE

FIELD

The present invention relates to an inspection apparatus, a sample for use in the inspection apparatus and a method usable for the inspection of a patterned part of a sample (e.g., a surface of a substrate being processed in the semiconductor industry).

BACKGROUND

A lithographic projection apparatus is used to image a pattern (e.g. in a mask) onto a substrate that is at least partially covered by a layer of radiation-sensitive material (resist). Prior to this imaging step, the substrate may undergo various procedures, such as priming, resist coating and a soft bake. After exposure, the substrate may be subjected to other procedures, such as a post-exposure bake (PEB), development, and a hard bake. These procedures are used as a basis to pattern an individual layer of a device, e.g. an IC. Such a patterned layer may then undergo various processes such as etching, ion-implantation (doping), metallization, oxidation, chemo-mechanical polishing, etc., all intended to finish off an individual layer. If several layers are required, then the whole procedure, or a variant thereof, will have to be repeated for each new layer. Eventually, an array of devices will be present on the substrate (wafer). These devices are then separated from one another by a technique such as dicing or sawing, whence the individual devices can be mounted on a carrier, connected to pins, etc. Each procedure or process may be followed by an inspection of the substrate in an inspection apparatus. With the inspection results, one may optimize or improve the procedures prior to the inspection or if a large part of the substrate is faulty, the patterned layer may be stripped off the substrate and the stripped patterned layer may be reapplied through exposure and/or other lithographic processing. Further information regarding lithographic processes used in, for example, the semiconductor industry can be obtained, for example, from the book "Microchip Fabrication: A Practical Guide to Semiconductor Processing", Third Edition, by Peter van Zant, McGraw Hill Publishing Co., 1997, ISBN 0-07-067250-4, incorporated herein by reference.

Inspection apparatus for surface inspection of substrates may measure properties like line width, pitch and critical dimension (CD) of the patterned layer. A common technique used to perform such inspection is known as "scatterometry". Methods of scatterometry are described in Raymond et al., "Multiparameter Grating Metrology Using Optical Scatterometry", J. Vac. Sci. Tech. B, Vol.15 no.2 361-368 1997 and Niu et al., "Specular Spectroscopic Scatterometry in DUV Lithography", SPIE Vol. 3677, 1999. In scatterometry, white light is reflected by a patterned parts of a sample (e.g., periodic structures) of a substrate and the resulting reflection spectrum at a given angle is detected. The pattern giving rise to the reflection spectrum is reconstructed, e.g. using Rigorous Coupled-Wave Analysis (RCWA) or by comparison to a library of patterns derived by simulation.

The monochromatic light response from a surface may be described in terms of four experimental properties:
1) The Transverse Magnetic Reflectivity (RTM) which is the zero order reflectivity of light having its polarization parallel to the plane of incidence.
2) The Transverse Electric Reflectivity (RTE) which is the zero order reflectivity of light having its polarization direction perpendicular to the plane of incidence.
3) The phase change (DTM) of the light in the zero order reflectivity having its polarization direction parallel to the plane of incidence.
4) The phase change (DTE) of the light in the zero order reflectivity having its polarization direction perpendicular to the plane of incidence.

With a technique called reflectometry, it is possible to measure the absolute values RTM and RTE. With another technique called ellipsometry, it is possible to measure the ratio of the two reflectivities (RTM/RTE) and the difference between the two phase changes (DTM/DTE). However, not with one or any combination of these techniques may all four of the above-referenced experimental parameters be determined. The reason is that only the difference of the two phases (DTM/DTE) is measured in ellipsometry and reflectivity does not provide any information about the phase. Thus, these techniques do not specifically measure both DTM and DTE.

SUMMARY

Accordingly, it would be advantageous, for example, to provide an improved inspection apparatus for inspecting samples.

According to an aspect of the invention, there is provided an inspection apparatus, comprising:
an radiation system configured to provide an radiation beam;
a beamsplitter configured to create, from the radiation beam, a first illumination beam and a second illumination beam directed to a planar reference part of a sample and a patterned part of the sample, respectively; and
a beam detector configured to detect a detection beam, the detection beam comprising a recombination of radiation scattered from the planar reference part and the patterned part.

According to an aspect of the invention, the radiation system comprises a first polarizer configured to generate an radiation beam having a certain polarization, the beam detector is configured to detect an intensity of different polarizations of the detection beam generated by a second polarizer, and the beamsplitter is a first polarization sensitive beamsplitter configured to create, from the radiation beam, first and second illumination beams with perpendicular polarizations. The radiation scattered from the planar reference part and the patterned part may be recombined by the first polarization sensitive beamsplitter to form the detection beam.

According to an aspect of the invention, there is provided a second polarization sensitive beamsplitter configured to recombine the radiation scattered from the planar reference part and the patterned part to form the detection beam. The first and/or second polarization sensitive beamsplitter may be a Wollaston prism or a Savert plate.

According to an aspect of the invention, the beam detector comprises a rotational polarizer.

According to an aspect of the invention, the radiation system is configured to provide an radiation beam with a broad wavelength and the beam detector comprises a wavelength analyzer configured to detect light intensity of the detection beam at different wavelengths.

According to an aspect of the invention, the wavelength analyzer comprises a grating or a prism configured to separate light with different wavelengths from the detection beam. The wavelength analyzer may be provided with a photosensitive array configured to detect the intensity of light present in the detection beam.

According to an aspect of the invention, the inspection apparatus may be provided with a sample table configured to hold the sample and to move with respect to the first and second illumination beams. The sample table may be configured to move the patterned part and the planar reference part from a first position where the patterned part and the planar reference part can be inspected with the first and second illumination beams respectively to a second position where the patterned part and the planar reference part can be inspected with the second and first illumination beams respectively.

According to an aspect of the invention, the first and second illumination beams have a direction substantially perpendicular to the surface of the patterned part of the sample.

According to an aspect of the invention, the first and second illumination beams have an incident angle larger than 0 degrees with respect to the normal of the surface of the patterned part of the sample. The detection beam may have a reflection angle larger than zero with respect to the normal of the detected surface of the planar reference part and the patterned part. The incident angle and the reflection angle may be substantially equal and both may be varied.

According to an aspect of the invention, the patterned part of the sample comprising a grating.

According to an aspect of the invention, the planar reference part of the sample comprises a planar stack having multiple layers.

According to an aspect of the invention, there is provided a sample for use in the inspection apparatus, the sample comprising a planar reference part and a patterned part on its surface.

According to an aspect of the invention there is provided, a method to inspect a patterned part of a sample, comprising:
 providing an radiation beam;
 creating, from the radiation beam, a first illumination beam and a second illumination beam directed to a planar reference part of the sample and a patterned part of the sample, respectively; and
 detecting a detection beam, the detection beam comprising a recombination of radiation scattered from the planar reference part and the patterned part.

According to an aspect of the invention, there is provided a method for inspecting a patterned part of a sample, comprising:
 illuminating a planar reference with a first illumination beam;
 illuminating the patterned part with a second illumination beam;
 recombining the first and the second illumination beams to form a first detection beam;
 detecting an optical property of the first detection beam;
 illuminating the planar reference with the second illumination beam;
 illuminating the patterned part with the first illumination beam;
 recombining the first and the second illumination beams to form a second detection beam;
 detecting an optical property of the second detection beam; and
 calculating properties of the patterned part of the sample using the detected properties of the first and second detection beams.

BRIEF DESCRIPTION OF THE DRAWINGS

Embodiments of the invention will now be described, by way of example only, with reference to the accompanying schematic drawings in which corresponding reference symbols indicate corresponding parts, and in which.

DETAILED DESCRIPTION

Figure 1:
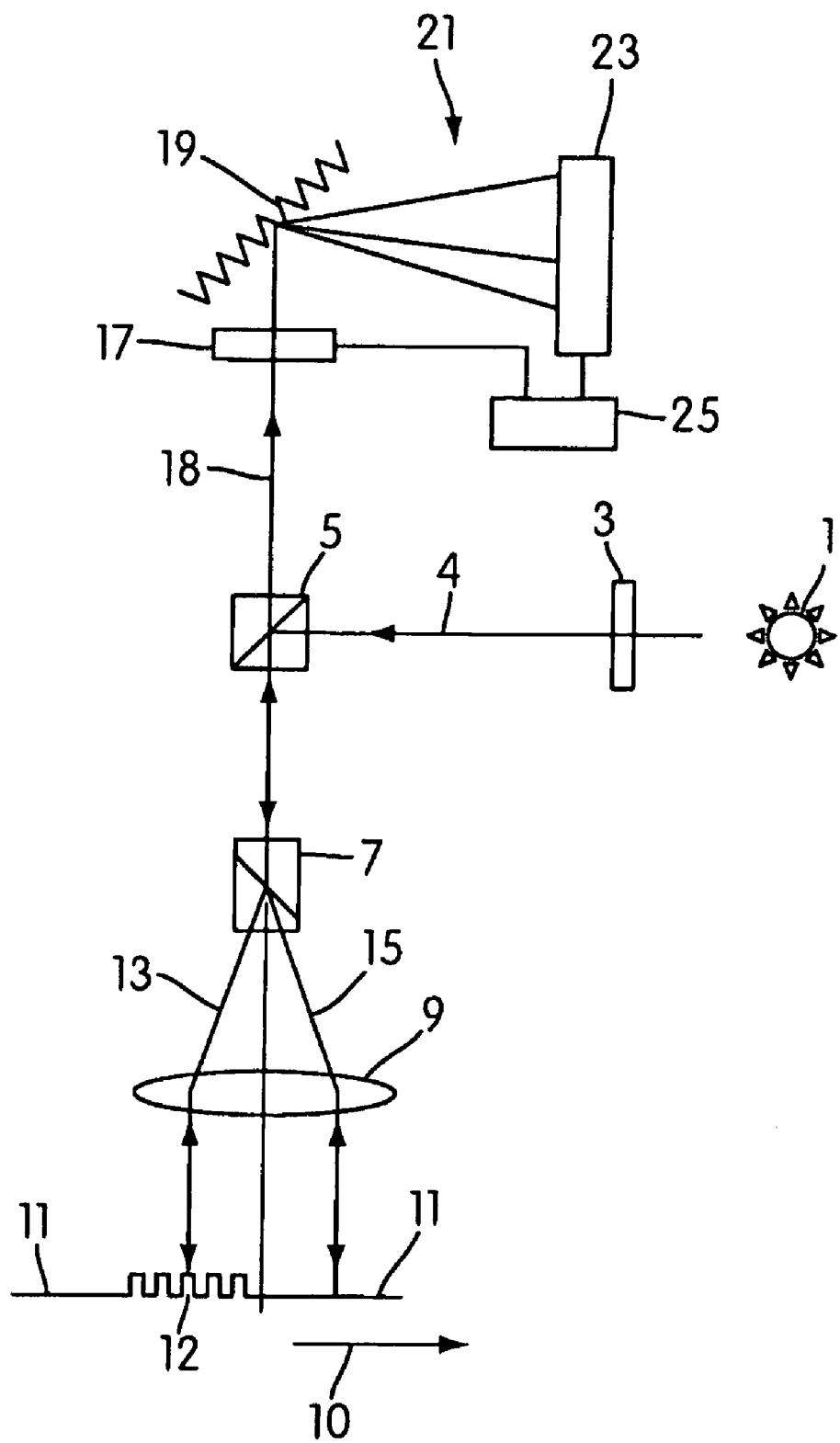
FIG. 1 depicts an inspection apparatus according to a first embodiment of the invention.

FIG. 1 schematically depicts an inspection apparatus according to a first embodiment of the invention having a so-called normal incident set up which means that the illumination beam is incident on the sample from a direction normal to the surface of the sample.

The inspection apparatus comprises:
 an radiation system configured to receive light from a source 1 (e.g., a broadband source like a light bulb) and comprising a first polarizer 3 configured to generate an radiation beam 4 having a broad wavelength and a known polarization;
 a beam detector provided with a polarizer 17 (e.g., a rotating polarizer capable of rotating the polarization of a beam 360 degrees under the control of a controller 25) and a wavelength analyzer 21 provided with a grating 19 (alternatively a prism may be used) which diffracts a detection beam 18 to a certain position on the detector 23 (e.g., a Charge Coupled Devices (CCD) array) dependent on the wavelength; and
 a beamsplitter 5 and a polarization sensitive beamsplitter 7 (e.g., a Wollaston prism or a Savert plate) configured to create first and second illumination beams 13, 15, each with an orthogonal linear polarization, from the radiation beam 4 and to direct the first illumination beam 13 to a patterned part 12 of the sample (e.g., a grating structure processed on silicon) and the second illumination beam 15 to a planar reference part 11 of the sample (e.g., bare silicon) so that the radiation scattered by the sample is recombined by the polarization sensitive beamsplitter 7 to form the detection beam 18 directed to the beam detector.

When inspecting a sample, light from the source 1 will go through the polarizer 3 which, for example, is rotated 45 degrees. The two components of the polarized light in the radiation beam 4 will therefore be linearly polarized which means that the two polarization components (TE, TM) are in phase and have the same amplitude. The beamsplitter 5 orients the radiation beam 4 towards the sample where after the polarization sensitive beamsplitter 7 creates two illumination beams 13, 15, each with a perpendicular polarization, from the radiation beam 4. The illumination beam 15 is directed to the planar reference part 11 of the sample (see FIG. 2), which may just be the bare silicon of a substrate, while the illumination beam 13 is directed to the patterned part 12 of the sample.

After normal incident scattering, the polarization sensitive beamsplitter 7 would recombine the two scattered beams into the detection beam 18. The light in the detection beam 18 would no longer be linearly polarized, as in the radiation beam 4, but rather would be elliptically polarized for each wavelength because the complex reflection coefficients of the patterned part 12 and the planar reference part 11 are different and therefore the polarization states are not anymore in phase and have a different amplitude.

The polarizer 17 and the wavelength analyzer 21 are used to measure the eccentricity and the orientation of the elliptically polarized light for each wavelength in the detection beam 18. By rotating the polarization in the polarizer 17, only light with a certain polarization direction is transmitted through the polarizer 17 to the diffraction grating. The diffraction grating 19 diffracts the light dependent on its wavelength to a certain part of the detector 23, which will measure the intensity of the light. The intensity of the eccentricity and the orientation of the elliptically polarized light present in the detection beam 18 for a certain wavelength can be calculated by the controller 25 with information about the direction of the polarization created by the polarizer 17 and the intensity received at the detector 23. The polarizer 17 rotates the polarization with an angle A and the detector measures the intensity as a function of the rotation angle A giving an intensity of the form:

$$\frac{I(A)}{I_0} = 1 + a*\text{Sin}(2A) + b*\text{Cos}(2A)$$

With this formula, one can trace down the two experimental numbers (the eccentricity of the ellipse a and its orientation with respect to the grating b) to the complex reflection coefficients of the mode coming on the grating and the planar reference part. If the reference is known, as would be the case when the reference is bare silicon, then one can calculate the complex reflection coefficient of the mode coming on the patterned part. If the light in the illumination beam 13 has a polarization parallel to the plane of incidence, the RTM and DTM can be measured.

A next step will be to move the sample in the direction of arrow 10 such that the first illumination beam 13 would be directed to another planar reference part 11 of the sample and the second illumination beam 15 would be directed to the patterned part of the sample 12. The second illumination beam 15 has an opposite polarization state as the first illumination beam 13 so that RTE and DTE properties of the grating can be measured. With these measurements, one would have access to all four parameters—RTM, DTM, RTE and DTE—of the patterned part of the sample.

Figure 2:
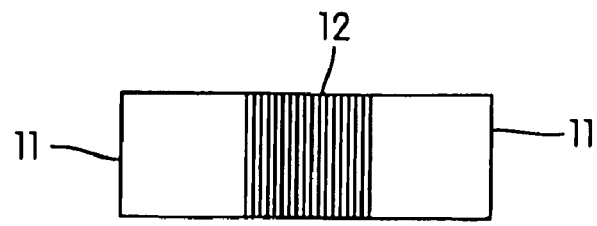
FIG. 2 depicts a dedicated sample for use in an inspection apparatus according to an embodiment of the invention.

FIG. 2 schematically depicts a sample with a patterned part 12 (e.g., a grating) positioned between two planar reference parts 11 according to an embodiment of the invention. The patterned part has a grating exposed on its surface and the planar reference part is just a planar surface. The planar surface may have had the same chemical processing steps as the patterned part except that during lithographic processing no features were patterned on the planar reference part. The planar reference part may also be bare silicon. An advantage of measuring the patterned part and the planar reference part of the sample simultaneously may be that the inspection apparatus will be only sensitive to the contributions not common between the planar reference part and the patterned part of the sample, i.e., the features in the patterned part. By having the planar reference part and the patterned part on the sample, the illumination and detection beams for both the planar reference part and the patterned part of the sample traverse through substantially same optical path which may make the apparatus less sensitive to vibrations and heat influences.

Figure 3:
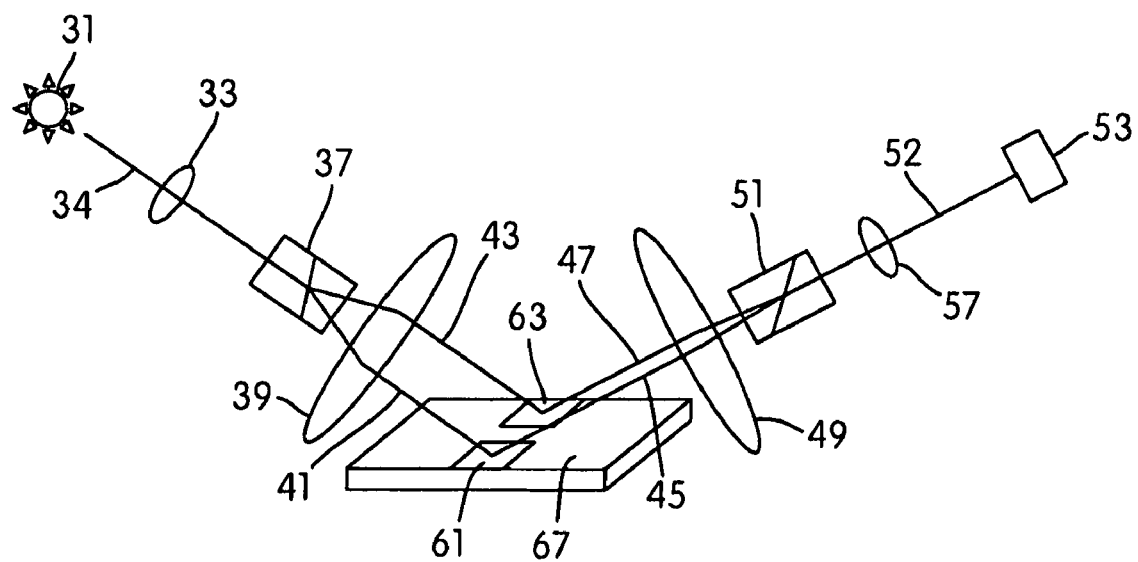
FIG. 3 depicts an inspection apparatus according to a second embodiment of the invention.

FIG. 3 schematically depicts an inspection apparatus according to a second embodiment of the invention in an oblique incidence set-up.

The inspection apparatus comprises:

an radiation system configured to receive light from a source 31 (e.g., a broadband source like a light bulb) and comprising a first polarizer 33 configured to generate an radiation beam 34 having a range of wavelengths and a known polarization;

a beam detector provided with a rotational polarizer 57 and a wavelength analyzer 53 configured to detect the polarization for different wavelengths of a detection beam 52; and a Wollaston prism 37 configured to configured to create first and second illumination beams 41, 43, each with a perpendicular polarization, from the radiation beam 34;

a lens 39 configured to focus the first and second illumination beam 41, 43 on the sample 67, where the beams 41, 43 would be scattered by a planar reference part 61 and a patterned part 63, respectively, of the sample 67; and a lens 49 configured to direct the first and second scattered beams 45, 47 to a second Wollaston prism 51, the second Wollaston prism 51 configured to recombine the two scattered beams 45, 47 into a detection beam 52.

Due to the scattering on the sample 67, the light in the detection beam 52 would no longer be linearly polarized, as in the radiation beam 34, but rather would be elliptically polarized for each wavelength because the complex reflection coefficients of the patterned part 63 and the planar reference part 61 are different and therefore the polarization states are not anymore in phase and have a different amplitude.

The rotating polarizer 57 and the wavelength analyzer 53 are used under the control of controller 59 to measure the eccentricity and the orientation of the elliptically polarized light for each wavelength in the detection beam 58. The four parameters—RTM, DTM, RTE and DTE of the patterned part of the sample—may then be determined as described above in relation to the first embodiment.

Advantageously, the inspection apparatus according to this second embodiment offers the freedom of changing the incident angle with respect to the sample so that RTM, DTM, RTE and DTE can be measured for a variety of incident angles. Another advantage of this second embodiment is that the first Wollaston prism 37 cannot reflect light from the radiation beam 34 directly into the beam detector while in the first embodiment of the inspection apparatus these reflections may occur.

While specific embodiments of the invention have been described above, it will be appreciated that the invention may be practiced otherwise than as described. The description above is intended to be illustrative, not limiting. Thus, it will be apparent to one skilled in the art that modifications may be made to the invention as described without departing from the scope of the claims set out below.

The invention claimed is:

1. An inspection apparatus, comprising:
   a beamsplitter configured to create, from a radiation beam, a first illumination beam and a second illumination beam directed to a planar reference part of a sample and a patterned part of the sample, respectively;
   a beam detector configured to detect a detection beam, the detection beam comprising a recombination of radiation reflected and/or scattered from the planar reference part and the patterned part and having an elliptical polarization, and the detection comprising a determination of information related to the eccentricity and/or the orientation of the elliptical polarization of the radiation in the detection beam; and
   a sample table configured to hold the sample and to move with respect to the first and second illumination beams, the sample table configured to move the patterned part and the planar reference part from a first position where the patterned part and the planar reference part, in use, receive the first and second illumination beams, respectively, to be inspected by the first and second illumination beams, to a second position where the patterned part and the planar reference part, in use, receive the second and first illumination beams, respectively, to be inspected by the second and first illumination beams.

2. The apparatus according to claim 1, comprising a first polarizer configured to generate, as the radiation beam, a polarized radiation beam having a certain polarization, the beam detector is configured to detect an intensity of different polarizations of the detection beam generated by a second polarizer, and the beamsplitter comprises a first polarization sensitive beamsplitter configured to create, from the polarized radiation beam, the first and second illumination beams with perpendicular polarizations.

3. The apparatus according to claim 2, wherein the first polarization sensitive beamsplitter is configured to recombine radiation reflected and/or scattered from the planar reference part and the patterned part to form the detection beam.

4. The apparatus according to claim 2, further comprising a second polarization sensitive beamsplitter configured to recombine radiation reflected and/or scattered from the planar reference part and the patterned part to form the detection beam.

5. The apparatus according to claim 2, wherein the first polarization sensitive beamsplitter comprises a Wollaston prism.

6. The apparatus according to claim 2, wherein the first polarization sensitive beamsplitter comprises a Savert plate.

7. The apparatus according to claim 2, wherein the beam detector comprises a polarizer configured to rotate polarization of the detection beam about an optical axis along which the detection beam travels.

8. The apparatus according to claim 1 further comprising a radiation system configured to provide the radiation beam with a broad range of wavelengths and the beam detector comprises a wavelength analyzer configured to detect light intensity of the detection beam at different wavelengths.

9. The apparatus according to claim 8 wherein the wavelength analyzer comprises a grating configured to separate light with different wavelengths from the detection beam.

10. The apparatus according to claim 8, wherein the wavelength analyzer comprises a prism configured to separate light with different wavelengths from the detection beam.

11. The apparatus according to claim 8, wherein the wavelength analyzer comprises a photosensitive array configured to detect the intensity of light present in the detection beam.

12. The apparatus according to claim 1, wherein the first and second illumination beams have a direction substantially perpendicular to the surface of the patterned part of the sample.

13. The apparatus according to claim 1, wherein the first and second illumination beams have an incident angle larger than 0 degrees with respect to the normal of the surface of the patterned part of the sample.

14. The apparatus according to claim 13, wherein the incident angle and a reflection angle of the first and second illumination beams are substantially equal.

15. The apparatus according to claim 13, wherein the apparatus is capable of varying the incident angle.

16. The apparatus according to claim 1, wherein the detection beam has a reflection angle larger than zero with respect to the normal of the surface of the patterned part.

17. The apparatus according to claim 1, wherein the patterned part of the sample comprising a grating.

18. The apparatus according to claim 1, wherein the planar reference part of the sample comprises a planar stack having multiple layers.

19. The apparatus according to claim 1 comprising a controller configured to determine (a) RTM, or (b) DTM, or (c) RTE, or (d) DTE, or any combination of (a)-(d) of the patterned part.

20. The apparatus according to claim 1, comprising a controller configured to determine DTM and DTE of the patterned part.

21. The apparatus according to claim 1, comprising a controller configured to determine only one of (a) RTM, or (b) DTM, or (c) RTE, or (d) DTE.

22. A sample for use in the apparatus according to claim 1, the sample having a planar reference part and a pattern part on its surface.

23. A method to inspect a patterned part of a sample, comprising:
  creating, from a radiation beam, a first illumination beam and a second illumination beam;
  positioning a sample at a first position such that the first illumination beam is directed to a planar reference part of the sample and the second illumination beam is directed to a patterned part of the sample;
  detecting a detection beam, the detection beam comprising a recombination of radiation reflected and/or scattered from the planar reference part and the patterned part and having an elliptical polarization, and the detecting comprising determining information related to the eccentricity and/or the orientation of the elliptical polarization of the radiation in the detection beam; and
  moving the sample from the first position , to a second position where the patterned part and the planar reference part receive the second and first illumination beams, respectively, to be inspected by the second and first illumination beams.

24. The method according to claim 23, comprising generating, as the radiation beam, a polarized radiation beam having a certain polarization, and wherein detecting the detection beam comprises detecting an intensity of different polarizations of the detection beam and creating the first and second illumination beams comprises creating first and second illumination beams with perpendicular polarizations from the polarized radiation beam.

25. The method according to claim 23 , further comprising providing the radiation beam with a broad range of wavelengths and wherein detecting the detection beam comprises detecting light intensity of the detection beam at different wavelengths.

26. The method according to claim 23, wherein the first and second illumination beams have a direction substantially perpendicular to the surface of the patterned part of the sample.

27. The method according to claim 23, wherein the first and second illumination beams have an incident angle larger than 0 degrees with respect to the normal of the surface of the patterned part of the sample.

28. The method according to claim 23, comprising determining and storing (a) RTM, or (b) DTM, or (c) RTE, or (d) DTE, or any combination of (a)-(d) of the patterned part.

29. The method according to claim 23, comprising determining and storing DTM and DTE of the patterned part.

30. A method for inspecting a patterned part of a sample, comprising:
  illuminating a planar reference with a first illumination beam;

illuminating the patterned part with a second illumination beam;

combining radiation from the first and the second illumination beams that has been reflected and/or scattered from the planar reference and the patterned part to form a second detection beam;

detecting an optical property of the first detection beam;

determining information related to an eccentricity and/or an orientation of an elliptical polarization of radiation in the first detection beam;

illuminating the planar reference with the second illumination beam;

illuminating the patterned part with the first illumination beam;

combing radiation from the first and the second illumination beam that has been reflected and/or scattered from the planar reference and the patterned part to from a second detection beam;

detecting an optical property of the second detection beam;

determining information related to an eccentricity and/or an orientation of an ellitical polarization of radiation in second detection beam;

calculating properties of the patterned part of the sample based on the determined information related to the eccentricities and/or the orientation of the elliptical polarization of radition in the first and second detection beams;and storing the calculated properties.

* * * * *